United States Patent [19]  [11] Patent Number: 4,701,531
Adaway                          [45] Date of Patent: Oct. 20, 1987

[54] CATALYZED ALKYLATION OF HALOPYRIDINATES IN THE ABSENCE OF ADDED ORGANIC SOLVENTS

[75] Inventor: Timothy J. Adaway, Midland, Mich.

[73] Assignee: The Dow Chemical Company, Midland, Mich.

[21] Appl. No.: 936,548

[22] Filed: Dec. 1, 1986

[51] Int. Cl.[4] .................. C07D 213/30; C07D 213/36; C07D 213/64
[52] U.S. Cl. .................................... 546/297; 546/301; 546/302
[58] Field of Search ............... 546/297, 302, 301, 296; 71/94

[56] References Cited

U.S. PATENT DOCUMENTS

| | | | |
|---|---|---|---|
| 3,969,360 | 7/1976 | Freedman | 546/297 |
| 4,235,621 | 11/1980 | Nishiyama et al. | 71/94 |
| 4,253,866 | 3/1981 | Schurter et al. | 71/94 |
| 4,254,262 | 3/1981 | Koike et al. | 546/287 |
| 4,309,547 | 1/1982 | Koch et al. | 546/301 |
| 4,596,599 | 6/1986 | Moriya et al. | 71/94 |

*Primary Examiner*—Alan L. Rotman
*Attorney, Agent, or Firm*—Joseph T. Majka; Ronald G. Brookens

[57] ABSTRACT

A process for preparing O-alkylated halopyridinate compounds is described. The process does not require the use of added organic solvents.

11 Claims, No Drawings

CATALYZED ALKYLATION OF HALOPYRIDINATES IN THE ABSENCE OF ADDED ORGANIC SOLVENTS

BACKGROUND OF THE INVENTION

O-alkylated halopyridinates are compounds known to possess excellent herbicidal properties. U.S. Pat. No. 3,969,360 teaches that the O-alkylated halopyridinates can be prepared by reacting an alkali metal halopyridinates in solid particulate form with a lower alkyl ester of α-chloro or bromoacetic acid (or propionic acid) in an inert organic liquid reaction medium under alkaline conditions and in the presence of a quaternary ammonium salt catalyst. Although this process generally achieves good yields, it has the disadvantage of utilizing organic solvents which must be separated from the reaction mixture. Separation of the organic solvents from the reaction mixture after formation of the desired product requires multiple steps and high energy requirements. After separation, the organic solvents require either waste disposal and/or recycling using an elaborate and expensive recycling apparatus. Another disadvantage of this process is that yields are detrimentally affected by amounts of water which would induce hydrolysis of the haloester in the reaction medium. It would be desirable to carry out the reaction of the alkali metal halopyridinate and the haloester in the presence of water without having to remove completely the water from the reaction mixture. It would also be desirable to employ a process for preparing O-alkylated halopyridinates which eliminates using added organic solvents.

Summary of the Invention

The present invention is directed to a process for preparing an O-alkylated halopyridinate compound of the formula

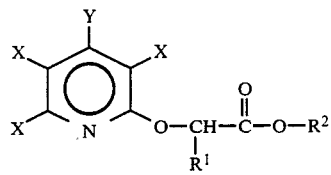

wherein
each X independently represents hydrogen or halogen;
Y is hydrogen, halogen or $-NR^3R^4$ wherein $R^3$ and $R^4$ are each independently hydrogen or lower alkyl;
$R^1$ is hydrogen or methyl; and
$R^2$ is lower alkyl;
comprising contacting an aqueous slurry containing a halopyridinate of the formula

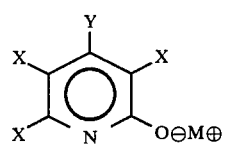

wherein M⊕ represents an alkali, alkaline earth metal or ammonium, with about an equimolar amount of a haloester of the formula

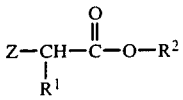

wherein
$R^1$ and $R^2$ are as defined hereinabove; and
Z is a leaving group selected from the group consisting of chloro, bromo, iodo, tosylate, mesylate and brosylate, in the presence of a catalytic amount of a phase transfer catalyst and in the absence of an added organic solvent; and recovering said O-alkylated halopyridinate compound.

As to the halopyridinate, preferably each X is chloro and Y is hydrogen. As to the haloester, it is preferred that $R^1$ is hydrogen, $R^2$ is ethyl or isopropyl, and Z is chloro or bromo. Preferably, the phase transfer catalyst is a quaternary ammonium salt, most preferably tetra n-butyl ammonium bromide.

The process of the present invention has the advantage of being able to utilize mixture containing alkali, alkaline earth metal or ammonium halopyridinate salt and water without having to add an organic solvent. Another advantage of the present invention is that it simplifies the preparation of O-alkylated halopyridinates by reducing the number of steps necessary for their preparation.

DETAILED DESCRIPTION OF THE INVENTION

The term "lower alkyl" is used in the present specification and in the appended claims to designate a straight or branched saturated hydrocarbon moiety (i.e., hydrocarbons having carbon-carbon single bonds) containing from 1 to 8 carbon atoms, such as, for example, methyl, ethyl, propyl, isopropyl, butyl, isobutyl, tertbutyl, pentyl, hexyl, and the like.

The term "phase transfer catalyst" is intended to mean a material which catalyzes a reaction by the transfer of one phase to another. Phase transfer catalysts suitable for carrying out the process of the present invention include the quaternary ammonium and phosphonium salts, ethers and tertiary amines, such as tributyl amine.

The quaternary ammonium and phosphonium salts suitable as catalysts include essentially any compound from the known class of quaternary ammonium and phosphonium salts can be used in the instant invention. Suitable quaternary ammonium and phosphonium salts may have a minimum solubility of at least about 1 weight percent in the liquid reaction medium at 25° C. and normally have a total aggregate carbon content of at least about 4 carbon atoms and preferably from about 12 to about 31 carbon atoms. The ammonium and phosphonium salts can be represented by the formula $R_1'R_2'R_3'R_4'Q^+A^-$, wherein $R^{1'}-R^{4'}$ and hydrocarbyl groups (e.g., alkyl, aryl, alkaryl, aralkyl, cycloalkyl, etc.) and $Q^+$ is a quaternized atom of nitrogen or phosphorus. Additionally, in $R_1'$ can join with $R_2'$ to form a 5- or 6-membered heterocyclic compound having at least one quaternized nitrogen or phosphorous atom in the ring and may also contain one non-adjacent atom of nitrogen, oxygen or sulfur within the ring. Typically, $R_1'-R_4'$ are hydrocarbyl groups of from 1 to about 12 carbon atoms. $A^-$ is an inert neutralizing anion and may be varied to convenience. By "inert" is meant inert in the instant process. Chloride and bromide are the preferred anions but other suitable anions include, for example, fluoride, iodide, bisulfate, acetate, tosylate, benzoate, and the like. The following compounds are illustrative: tetraalkyl ammonium salts, such as tetra-n-butyl-, tetrahexyl-, tri-n-butyl-methyl-, cetyltrimethyl-, trioctylmethyl- and tridecylmethyl ammonium chlorides, bromides, bisulfates, tosylates, etc.; aralkylammonium salts, such as tetrabenzylammonium chloride, benzyltrimethyl-, benzyltriethyl-, benzyltributyl-, and phenethyltrimethylammonium chlorides, bromides, etc.; arylammonium salts, such as triphenylmethylammonium fluoride, chloride or bromide, N,N,N-trimethylanilinium bromide, N,N-diethyl-N-methylanilinium bisulfate, trimethylnaphthylammonium chloride, p-methylphenyltrimethylammonium chloride or tosylate, etc.; 5- and 6-membered heterocyclic compounds containing at least one quaternized nitrogen atom in the ring, such as N-methylpyridinium chloride or methyl sulfate, N-hexyl pyridinium iodide, (4-pyridyl)-trimethylammonium chloride, 1-methyl-1-azabicyclo [2.2.1] heptane bromide, N,N-dibutylmorpholinium chloride, N-ethylthiazolium chloride, N-butylpyrrolium chlorides, etc. and the corresponding phosphonium salts and other like compounds.

The ammonium salts are currently preferred over the phosphonium salts due to cost and commercial availability. The suitable catalysts are benzyltriethyl-, tetra-n-butyl and tri-n-butylmethyl ammonium salts, most preferably tetra-n-butyl.

The phase transfer catalysts are used in the process in small but catalytic amounts. For example, amounts from about 0.1 to about 20 mole percent, based on the reactants, are suitable but amounts of from about 0.1 to about 10 mole percent are generally preferred more preferably from about 1 to about 5 mole percent.

A base and/or buffer is used to prepare and to maintain the alkali metal halopyridinate reactant in its anionic or salt form before and during its reaction with the haloester. The base or buffer also maintains the stability of the haloester and the O-alkylated halopyridinate (I) derived therefrom against hydrolysis. The base and/or buffer can be represented by the formula

MT wherein

M independently represents alkali (Na, K, Li) and alkaline (Ca, Mg) earth metals, or ammonium (NH4) or any suitable counter cation; and T independently represents hydroxide (OH), bicarbonate (HCO3), carbonate (CO3), phosphate (PO4) hydrogen phosphates (HPO4), dihydrogen phosphate (H2PO4), and borate (BO3) or any other anion suitable for providing the proper pH.

The amount of base and/or buffer employed in the present process can range from about 1 to about 1.5 moles base and/or buffer per one mole of halopyridinol (moles base or buffer:moles pyridinol), preferably about 1.1:1.

The halopyridinates of Formula (II) can be contacted with the haloester of Formula (III) in about equimolar ratios ranging from about 0.90:1 to about 1.5:1, more preferably about 1.15:1 (haloester:halopyridinate).

The contacting of the halopyridinate and the haloester is carried out at temperatures ranging from about ambient to about 120 degrees Centigrade (°C.) preferably from 60° to about 80° C. The contacting is normally carried out at ambient pressures with stirring or other means of agitation.

The term "slurry" is meant to mean a homogeneous or heterogeneous mixture of water and the requisite halopyridinate of Formula (II).

The amount of water in association with the halopyridinate is such that the halopyridinate level in the aqueous slurry can range from about 5 percent to about 95 percent, preferably from about 60 to 80 percent by weight. The aqueous slurry may contain crude products or impurities which do not adversely affect the reaction between the halopyridinate and the haloester. Such materials can include by-products from the in situ preparation of the pyridinate starting materials, which contain sodium chloride or sodium bromide. Generally, as the hydrolytic stability of the haloester decreases, the lesser the amount of water is used. For example, less water is used with the methyl ester, which is more susceptible to hydrolysis than the ethyl ester, etc.

The halopyridinates of Formula (II) are known to those skilled in the art, and can be prepared by contacting the requisite halopyridinol with about 10 percent by weight NaOH, giving an aqueous mixture containing the desired alkali metal halopyridinate. The amount of water associated with the halopyridinate can be reduced to the desired level by conventional procedures such as water stripping or filtration.

The alkyl esters of α-chloro or bromoacetic acid (or propionic acid) of Formula (III) are likewise well known. The alkyl esters of α-chloroacetic acid are the most preferred reactants and the ethyl and isopropyl ester of α-chloroacetic acid are the most preferred.

The alkylation reaction can be carried out by mixing the halopyridinate and catalyst with a slight excess of the haloacetate ester (<30 mole percent excess) and heating. The order of mixing of the components is not critical to practicing the present invention. When the water content is less than about 35 percent relative to the pyridinate, then it is beneficial to add the pyridinate slowly to the rest of the components to avoid the high viscosity that would initially be generated if mixed all at once. Because no organic solvent is added to the reaction mixture, it is desirable that the requisite reaction temperature be maintained above the melting point of the crude product.

After the reaction is completed, the desired O-alkylated halopyridinate compound of Formula I is recovered by conventional recovery procedures such as phase separation, distillation or recrystallization. Any catalyst residues and inorganic salts associated in or with the aqueous phase are typically removed by a simple wash, ion-exchange treatment, filtration, washing and the like.

The following examples illustrate the present invention in a manner by which it can be practiced but, as such, should not be construed as limitations upon the overall scope of the same.

EXAMPLE 1

Preparation of ethyl 2-(3,5,6-trichloro-2-pyridinyloxy)acetate

To a 250 milliliters (ml) round bottom flask equipped with an air-driven stirrer, thermowell, and reflux condenser, is charged 96.5 grams (g) (0.79 moles) ethyl 2-chloroacetate (ETCA), 5.7 g (0.018 moles) tetra n-butyl ammonium bromide (TBAB), 4 g (0.038 moles)

sodium carbonate (Na$_2$CO$_3$), and 3 g (0.036 moles), sodium bicarbonate (NaHCO$_3$). The mixture is heated to a temperature of 70° C. To the mixture is added 162 g (0.68 moles) of 92.5 percent sodium 3,5,6-trichloro-2-pyridinate (NaTCP) (containing 7.5 percent water) over a period of 1.5 hours. Three hours following addition of the sodium 3,5,6-trichloro-2-pyridinate, the conversion of sodium 3,5,6-trichloro-2-pyridinate is analyzed to be 100 percent. The mixture is diluted with 250 ml of water heated to 70° C. Phase separation of the mixture gives 196.7 g of a crude organic product. This crude product assays at 90.1 percent ethyl 2-(3,5,6-trichloro-2-pyridinyloxy)acetate with a 92.1 percent yield. The total accountability of sodium 3,5,6-trichloro-2-pyridinate derived compounds in the crude product is 98 percent.

EXAMPLE 2

In a reaction equipment set up similar to that as described in Example 1 is mixed 90.1 g (0.37 moles) of 90.5 percent sodium 3,5,6-trichloro-2-pyridinate, 21.6 g (0.37 moles) sodium chloride (NaCl), 71.9 g water, to give a 56 percent by weight halopyridinate aqueous slurry. To this slurry is added 3.12 g (0.0097 moles) tetra n-butyl ammonium bromide, 1.25 g NaHCO$_3$, and 2.5 g NaCO$_3$. The slurry is heated to 65° C. and 53 g (0.433 moles) ethyl 2-chloroacetate is added. Two and one half hours later the temperature is increased to 70° C. After a total of 11 hours of reaction, the reaction mixture is analyzed at 99.8 percent conversion of the sodium 3,5,6-trichloro-2-pyridinate and is diluted with 125 ml of hot water. Phase separation results in 105.4 g of a crude organic product. This crude product assays at 93.1 percent ethyl 2-(3,5,6-trichloro-2-pyridinyloxy)acetate with a 93.2 percent crude yield. The accountability of sodium 3,5,6-trichloro-2-pyridinate based products is 99 percent.

EXAMPLE 3

In a reaction equipment set up similar to that as described in Example 1 is mixed 60 g (0.21 moles) of 77 percent sodium 3,5,6-trichloro-2-pyridinate, 64 g (1.09 moles) NaCl, 171 g of water, to give a 21 percent by weight halopyridinate aqueous slurry. To this slurry is added 2.65 g (0.008 moles) of TBAB, and 2.65 g Na$_2$CO$_3$. When the slurry reaches a temperature of 75° C., 31.7 g (0.26 moles) ethyl 2-chloroacetate is added. Four hours later the temperature of the reaction mixture is increased to 80° C. After a total of 7 hours of reaction, the mixture is analyzed at 98 percent conversion of sodium 3,5,6-trichloro-2-pyridinate. The mixture is then diluted with 100 ml of water. Phase separation gives 57.4 g of a crude organic product which assays at 89.9 percent ethyl 2-(3,5,6-trichloro-2-pyridinyloxy)acetate for a 86.9 percent crude yield. Total accountability in the crude product of sodium 3,5,6-trichloro-2-pyridinate based compounds is 95 percent...

EXAMPLE 4

In a reaction equipment set up similar to that as described in Example 1 is mixed 36.6 g (0.15 moles) 90.5 percent sodium 3,5,6-trichloro-2-pyridinate, 8.9 g (0.15 moles) NaCl, and 120 g of water to give a 22 percent by weight halopyridinate aqueous slurry. To this slurry is added 2.9 g NaHCO$_3$, 2.35 g (0.0045 moles) 61.5 percent tetra n-butyl ammonium bromide and 26.2 g (0.19 moles) isopropyl 2-chloroacetate. The mixture is heated at 70° C. for 24 hours to reach 98 percent conversion. About 0.5 g Na$_2$CO$_3$ is added and the heating continues for an additional two hours to obtain 100 percent conversion. Phase separation gives 45.6 g of a crude organic product which assays at 89 percent isopropyl 2-(3,5,6-trichloro-2-pyridinyloxy)acetate, for a 90.6 percent crude yield.

EXAMPLE 5

In a reaction equipment set up similar to that as described in Example 1 is mixed 25 g (0.1 moles) 90.5 percent sodium 3,5,6-trichloro-2-pyridinate, 10.8 g (0.2 moles) sodium bromide (NaBr), and 90 g H$_2$O to give a 20 percent by weight halopyridinate aqueous slurry. To this slurry is added 1 g (0.0031 moles) tetra n-butyl ammonium bromide, 1 g Na$_2$CO$_3$, and 21.7 g (0.13 moles) ethyl 2-bromoacetate. After two hours at 72° C. the conversion is 100 percent. Phase separation gives 30.6 g of an organic product which assays at 89 percent ethyl 2-(3,5,6-trichloro-2-pyridinyloxy)acetate, a 93.4 percent crude yield. The total accountability of sodium 3,5,6-trichloro-2-pyridinate based compounds is 99 percent.

EXAMPLE 6

In a reaction equipment set up similar to that described in Example 1 is mixed 25.2 g (0.105 moles) 90.5 percent sodium 3,5,6-trichloro-2-pyridinate, 6.2 g (0.105 moles) NaCl, and 90 g H$_2$O to give a 20 percent by weight halopyridinate aqueous slurry. To this slurry is added 1.5 g Na$_2$CO$_3$, 2 g (0.0054 moles) tetra n-butyl ammonium iodide, and 16.1 g (0.131 moles) ethyl 2-chloroacetate. The conversion of sodium 3,5,6-trichloro-2-pyridinate to ethyl 2-(3,5,6-trichloro-2-pyridinyloxy)acetate after 7 hours of reaction at 70° C. is 96 percent.

EXAMPLE 7

In a reaction equipment set up similar to that described as Example 1 is mixed 25.2 g (0.105 moles) 90.5 percent sodium 3,5,6-trichloro-2-pyridinate, 6.2 g (0.105 moles) NaCl, and 90 g water to give a 20 percent by weight halopyridinate aqueous slurry. To this slurry is added 1.5 g Na$_2$CO$_3$, 16 g (0.131 moles) ethyl 2-chloroacetate, and 10.1 g (0.0125 moles) polymeric catalyst. The polymeric catalyst is made by reacting a chloromethylated macroreticular cross-linked polystyrene with tri-n-butyl amine, thus giving a benzyl tri-n-butyl ammonium chloride catalytic site. The concentration of active sites is calculated to be 1.25 mmol/g. The conversion of sodium 3,5,6-trichloro-2-pyridinate to ethyl 2-(3,5,6-trichloro-2-pyridyloxy)acetate after three hours at 80° C. is 98 percent.

What is claimed is:

1. A process for preparing an O-alkylated halopyridinate compound of the formula

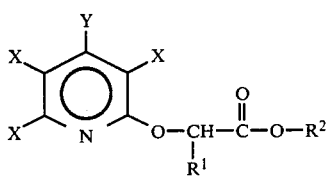

(I)

wherein
each X independently represents hydrogen or halogen;

Y is hydrogen, halogen or -NR$^3$R$^4$ wherein R$^3$ and R$^4$ are each independently hydrogen or lower alkyl;

R$^1$ is hydrogen or methyl; and

R$^2$ is lower alkyl;

comprising contacting an aqueous slurry containing a halopyridinate of the formula

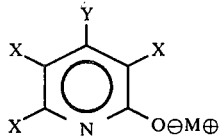
(II)

wherein M⊕ represents an alkali, alkaline earth metal or ammonium, with about equimolar amounts of a haloester of the formula

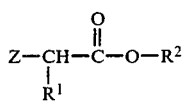
(III)

wherein

R$^1$ and R$^2$ are as defined hereinabove; and

Z is a leaving group selected from the group consisting of chloro, bromo, iodo, tosylate, mesylate and brosylate, in the presence of a catalytic amount of a phase transfer catalyst and in the absence of an added organic solvent; and recovering said O-alkylated halopyridinate compound.

2. The process of claim 1 wherein, in the halopyridinate, each X is chloro and Y is hydrogen.

3. The process of claim 1 wherein as to the haloester, R$^1$ is hydrogen, R$^2$ is ethyl or isopropyl and Z is chloro or bromo.

4. The process of claim 1 wherein the halopyridinate and haloester are stabilized with a buffer.

5. The process of claim 4 wherein the buffer is carbonate.

6. The process of claim 1 wherein the phase transfer catalyst is a quaternary ammonium salt.

7. The process of claim 6 wherein the quaternary ammonium salt is tetra-n-butyl ammonium bromide.

8. The process of claim 1 wherein contacting of the halopyridinate and the haloester is carried out at a temperature in the range from about ambient to about 120° Centigrade.

9. The process of claim 8 wherein the temperature is in the range of about 60° to about 80° C.

10. The process of claim 1 wherein the halopyridinate level in the aqueous slurry is in the range from about 5 to about 95 percent by weight.

11. The process of claim 10 wherein the halopyridinate level in the aqueous slurry is in the range from about 60 to about 80 percent by weight.

* * * * *